United States Patent [19]

Eistetter et al.

[11] 4,324,796
[45] Apr. 13, 1982

[54] SUBSTITUTED OXIRANECARBOXYLIC ACIDS, THEIR USE AND MEDICAMENTS CONTAINING THEM

[75] Inventors: Klaus Eistetter, Constance; Erich Rapp, Radolfzell, both of Fed. Rep. of Germany

[73] Assignee: BYK Gulden Lomberg Chemische Fabrik Gesellschaft mit beschränkter Haftung, Constance, Fed. Rep. of Germany

[21] Appl. No.: 182,934

[22] Filed: Sep. 2, 1980

[30] Foreign Application Priority Data

Sep. 7, 1979 [SU] U.S.S.R. ................ 8068/79

[51] Int. Cl.³ .............. C07D 303/48; A61K 31/335
[52] U.S. Cl. ................ 424/278; 260/348.58; 260/348.49; 562/495; 562/465; 560/104; 560/55
[58] Field of Search ............ 260/348.58, 348.49; 424/278

[56] References Cited

U.S. PATENT DOCUMENTS 4,132,719 1/1979 Mohrbacher .............. 260/348.48
4,132,720 1/1979 Mohrbacher .............. 260/348.61
4,196,300 4/1980 Mohrbacher et al. ......... 549/90

FOREIGN PATENT DOCUMENTS 1551078 8/1979 United Kingdom .

OTHER PUBLICATIONS

P.de Mayo, Can. Jour. Chem., vol. 45 (1967) pp. 2177-2190.
F. Oesch et al., Biochemistry, vol. 10, No. 26 (1971) pp. 4858-4866.

*Primary Examiner*—Norma S. Milestone
*Attorney, Agent, or Firm*—Berman, Aisenberg & Platt

[57] ABSTRACT

Substituted oxiranecarboxylic acids of the formula

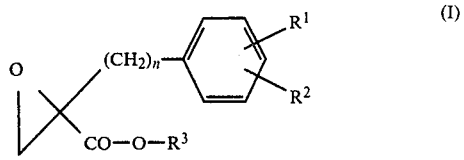

wherein
 $R^1$ denotes a hydrogen atom (—H), a halogen atom, a hydroxyl group, a lower alkyl group, a lower alkoxy group or a trifluoromethyl group,
 $R^2$ has one of the meanings of $R^1$,
 $R^3$ denotes a hydrogen atom (—H) or a lower alkyl group and
 n denotes an integer from 1 to 5, and
the salts of the acids are new compounds. They display a hypoglycaemic action in warm-blooded animals. Processes for the preparation of the new compounds and of the intermediate products required for their preparation are described.

21 Claims, No Drawings

SUBSTITUTED OXIRANECARBOXYLIC ACIDS, THEIR USE AND MEDICAMENTS CONTAINING THEM

TECHNICAL FIELD

The invention relates to substituted oxiranecarboxylic acids, processes for their preparation, their use and medicaments containing them.

BACKGROUND

Phenyloxiranecarboxylic acid esters, for example 2-phenyloxirane-2-carboxylic acid ethyl ester, inter alia, are within the scope of an investigation into the ability of substituted cyclic compounds (with a three-membered ring) to serve as a substrate or inhibitor for epoxide hydrase from guinea pig liver microsomes [F. Oesch et al., Biochem. 10 (1971) No. 26, 4,858-66]. Reaction of methyl N-acetyl isatoate with an excess of diazomethane yielded methyl 2-(o-acetamidobenzyl)glycidate in the course of the elucidation of the constitution of isamic acid [P. de Mayo and J. J. Ryan, Can.J.Chem. 45 (1967) 2177-2190]. Certain substituted oxiranecarboxylic acids have now been found to be pharmaceutically-active compounds with a specific action.

SUMMARY OF THE INVENTION

Pharmaceutically-active substituted oxiranecarboxylic acids, ω-(optionally substituted)phenylalkylene-α-methylenecarboxylic acids, their pharmacologically-acceptable salts and their lower alkyl esters have a hypoglycemic and hypoketonemic activity which makes them useful for the prophylaxis and treatment of disorders, such as diabetes, based on glucose and fat metabolism. The compounds are administered enterally or parenterally in conventional dosage forms to those subject to or afflicted with such disorders. The dosage forms ordinarily comprise compositions in which the active ingredient is in admixture with a suitable excipient or carrier.

The following types of acids are illustrative of that part of the compound aspect of this invention; corresponding salts and lower alkyl esters are readily appreciated by any artisan:

2-[ω-phenyl($C_{1-8}$)alkylene]oxirane-2-carboxylic acid,
2-[ω-(monosubstituted)phenyl($C_{1-8}$)alkylene]oxirane-2-carboxylic acid,
2-[ω-(disubstituted)phenyl($C_{1-8}$)alkylene]oxirane-2-carboxylic acid,
α-methylene-ω-phenylheptanoic acid,
ω-(m- or p-chloro)phenyl($C_{4-6}$)alkylene-α-methylenecarboxylic acid and
α-methylene-ω-(m- or p-trifluoromethyl)phenylheptanoic acid.

DETAILS

More particularly, the invention relates to substituted oxiranecarboxylic acids of the formula

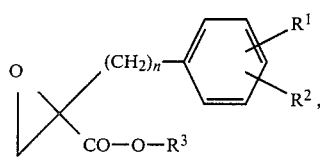

wherein $R^1$ denotes a hydrogen atom (—H), a halogen atom, a hydroxyl group, a lower alkyl group, a lower alkoxy group or a trifluoromethyl group,
$R^2$ has one of the meanings of $R^1$,
$R^3$ denotes a hydrogen atom (—H) or a lower alkyl group and
n denotes an integer from 1 to 8, and
salts of the carboxylic acids.

The lower alkyl groups include straight-chain and branched alkyl radicals with from 1 to 4 carbon atoms. Examples of straight-chain alkyl radicals are the methyl, ethyl, n-propyl and n-butyl radical, of which those with 1 or 2 carbon atoms are preferred. Examples of branched alkyl radicals are the isopropyl, isobutyl and sec.-butyl radical, of which that with 3 carbon atoms is preferred. Alkyl radicals in lower alkoxy groups are similarly both straight-chain and branched lower alkyl groups. The methoxy group is the preferred lower alkoxy group.

Halogen atoms are fluorine, chlorine and bromine atoms, of which fluorine and, in particular, chlorine are preferred.

Substituents $R^1$ and $R^2$ are preferably in the metaposition or para-position.

Salts include those with either an inorganic or an organic base. Pharmacologically-unacceptable salts are readily converted into pharmacologically-, that is to say biologically-, acceptable salts (which are preferred salts according to the invention) by conventional methods. Cations used for salt formation are, advantageously, those of alkali metals, alkaline-earth metals or earth metals, but cations corresponding to organic nitrogen bases, such as amines, aminoalkanols, amino-sugars and basic aminoacids, are optionally used.

Exemplary salts are those of lithium, sodium, potassium, magnesium, calcium, aluminum, ethylenediamine, dimethylamine, diethylamine, morpholine, piperidine, piperazine, N-(lower alkyl)piperazine (for example N-methylpiperazine), methylcyclohexylamine, benzylamine, ethanolamine, diethanolamine, triethanolamine, tris-(hydroxymethyl)aminomethane, 2-amino-2-methyl-propanol, 2-amino-2-methyl-1,3-propanediol, glucamine, N-methylglucamine, glucosamine, N-methylglucosamine, lysine, ornithine, arginine and quinoline.

Substituted oxiranecarboxylic acids I* of formula I, wherein $R^1$ and $R^2$ are in the meta-position or para-position and
$R^1$ denotes a hydrogen atom (—H), a chlorine atom, a methyl group, a methoxy group or a trifluoromethyl group,
$R^2$ denotes a hydrogen atom (—H) or a chlorine atom,
$R^3$ denotes a hydrogen atom (—H) or a lower alkyl group and
n denotes an integer from 3 to 7, and
salts of the carboxylic acids form an embodiment of the invention.

Substituted oxiranecarboxylic acids I** of formula I, wherein $R^1$ and $R^2$ are in the meta-position or para-position and
$R^1$ denotes a hydrogen atom (—H), a chlorine atom or a trifluoromethyl group,
$R^2$ denotes a hydrogen atom (—H),
$R^3$ denotes a hydrogen atom (—H), a methyl group or an ethyl group and
n denotes 3 or 4, and pharmacologically-acceptable salts of the carboxylic acids with an inorganic or organic base form a preferred embodiment of the invention.

Substituted oxiranecarboxylic acids I* (wherein $R^1$, $R^2$ and $R^3$ have the same meanings as for embodiment I, but n denotes 5) and the pharmacologically-acceptable salts of these carboxylic acids form a particularly preferred embodiment of the invention.

Examples of compounds according to the invention are:
2-(4-chlorobenzyl)oxirane-2-carboxylic acid ethyl ester,
2-(3-chlorobenzyl)oxirane-2-carboxylic acid methyl ester,
2-(4-fluorobenzyl)oxirane-2-carboxylic acid isopropyl ester,
2-[2-(4-chlorophenyl)ethyl]oxirane-2-carboxylic acid n-butyl ester,
2-[2-(4-methoxyphenyl)ethyl]oxirane-2-carboxylic acid methyl ester,
2-[2-(3-trifluoromethylphenyl)ethyl]oxirane-2-carboxylic acid ethyl ester,
2-[3-(3-fluorophenyl)propyl]oxirane-2-carboxylic acid ethyl ester,
2-[3-(4-bromophenyl)propyl]oxirane-2-carboxylic acid methyl ester,
2-[3-(3-methoxyphenyl)propyl]oxirane-2-carboxylic acid sec.-butyl ester,
2-{3-[4-(n-butoxy)phenyl]propyl}oxirane-2-carboxylic acid ethyl ester,
2-[3-(3-isopropoxyphenyl)propyl]oxirane-2-carboxylic acid isopropyl ester,
2-[4-(3-fluorophenyl)butyl]oxirane-2-carboxylic acid methyl ester,
2-[4-(3-trifluoromethylphenyl)butyl]oxirane-2-carboxylic acid n-butyl ester,
2-[4-(3-bromophenyl)butyl]oxirane-2-carboxylic acid ethyl ester,
2-[4-(4-chlorophenyl)butyl]oxirane-2-carboxylic acid n-propyl ester,
2-[4-(3,4-dichlorophenyl)butyl]oxirane-2-carboxylic acid ethyl ester,
2-[4-(3-chloro-4-methylphenyl)butyl]oxirane-2-carboxylic acid methyl ester,
2-[4-(4-ethoxyphenyl)butyl]oxirane-2-carboxylic acid ethyl ester,
2-[5-(4-methoxyphenyl)pentyl]oxirane-2-carboxylic acid ethyl ester,
2-[5-(3-trifluoromethylphenyl)pentyl]oxirane-2-carboxylic acid n-butyl ester,
2-[5-(4-methylphenyl)pentyl]oxirane-2-carboxylic acid methyl ester,
2-[5-(3-chlorophenyl)pentyl]oxirane-2-carboxylic acid isobutyl ester,
2-[5-(4-methoxyphenyl)pentyl]oxirane-2-carboxylic acid ethyl ester,
2-[6-(4-fluorophenyl)hexyl]oxirane-2-carboxylic acid ethyl ester,
2-[6-(3-trifluoromethylphenyl)hexyl]oxirane-2-carboxylic acid methyl ester,
2-[6-(3,4-dichlorophenyl)hexyl]oxirane-2-carboxylic acid n-butyl ester,
2-[6-(4-chlorophenyl)hexyl]oxirane-2-carboxylic acid isopropyl ester,
2-[7-(3-fluorophenyl)heptyl]oxirane-2-carboxylic acid ethyl ester,
2-[7-(4-trifluoromethylphenyl)heptyl]oxirane-2-carboxylic acid ethyl ester,
2-[7-(3-chloro-4-methylphenyl)heptyl]oxirane-2-carboxylic acid methyl ester,
2-[7-(3-chlorophenyl)heptyl]oxirane-2-carboxylic acid n-propyl ester,
2-[8-(4-fluorophenyl)octyl]oxirane-2-carboxylic acid ethyl ester,
2-[8-(3-trifluoromethylphenyl)octyl]oxirane-2-carboxylic acid methyl ester,
2-[8-(3,4-dichlorophenyl)octyl]oxirane-2-carboxylic acid ethyl ester and
2-[8-(4-chlorophenyl)octyl]oxirane-2-carboxylic acid isobutyl ester,
the corresponding oxirane-2-carboxylic acids and salts thereof with inorganic and organic bases.

Preferred representatives are:
2-[3-(3-chlorophenyl)propyl]oxirane-2-carboxylic acid ethyl ester,
2-[3-(4-chlorophenyl)propyl]oxirane-2-carboxylic acid ethyl ester,
2-[3-(3-trifluoromethyl-phenyl)propyl]oxirane-2-carboxylic acid ethyl ester,
2-(5-phenylpentyl)oxirane-2-carboxylic acid ethyl ester,
2-[5-(4-chlorophenyl)pentyl]oxirane-2-carboxylic acid ethyl ester, the corresponding oxirane-2-carboxylic acids and pharmacologically acceptable salts thereof.

The substituted oxiranecarboxylic acids of formula I and of embodiments I*, I and I* have a chirality center. The invention includes the racemates, the enantiomers and mixtures thereof.

The compounds according to the invention have valuable pharmacological properties which render them commercially valuable. They have a hypoglycemic and hypoketonemic action.

Because of their advantageous activity, the substituted oxiranecarboxylic acids of formula I (including embodiments I*, I and I*) and their pharmacologically-acceptable salts, are suitable in human and veterinary medicine for the treatment and prophylaxis of illnesses based on glucose and fat metabolism disorders. Prediabetic conditions are treated for prevention of the manifestation of diabetes; manifest diabetes, for example diabetes in adults, and labile diabetes in young persons and diseases which are accompagnied by an increased production of ketones are treated for control and symptom alleviation.

The invention thus also relates to a method for combating such illnesses by administration of compounds according to the invention to those subject to or afflicted with disorders of the indicated type. The invention furthermore relates to the use of compounds according to the invention in combating these illnesses.

Moreover, the invention relates to medicaments which contain one or more substituted oxiranecarboxylic acids of formula I,
wherein
$R^1$ denotes a hydrogen atom (—H), a halogen atom, a hydroxyl group, a lower alkyl group, a lower alkoxy group or a trifluoromethyl group,
$R^2$ has one of the meanings of $R^1$,
$R^3$ denotes a hydrogen atom or a lower alkyl group and
n denotes an integer from 1 to 8, and/or
pharmacologically-acceptable salts of the acids with inorganic or organic bases.

Medicament embodiments include those which contain substituted oxiranecarboxylic acids I*, I and I* and/or pharmacologically-acceptable salts of such acids with inorganic or organic bases.

The invention also encompasses the use of the compounds according to the invention for preparing medicaments for combating the noted illnesses.

The medicaments are conventionally prepared by known processes. As medicaments, the new compounds are employed as such or in combination with suitable pharmaceutical excipients. When the new pharmaceutical formulations contain pharmaceutical excipients in admixture with or in addition to one or more active compounds, the content of active compound is from 1 to 95, preferably from 15 to 85, percent by weight of the total.

According to the invention, the active compounds are used in the field of human medicine in any desired form, for example systemically, provided that sufficient levels of active compound are established and maintained in the blood or tissue. This is achieved, for example, by oral or parenteral administration in suitable doses. The pharmaceutical formulation of the active compound is advantageously in the form of unit doses appropriate for the desired mode of administration. A unit dose is, for example, in the form of a tablet, a dragee, a capsule, a suppository or a measured volume of a powder, of a granular material, of a solution, of an emulsion or of a suspension.

"Unit dose" for the purpose of the present invention means a physically-determined unit which contains an individual amount of active ingredient in combination with a pharmaceutical excipient, the content of active compound in the unit dose corresponding to a fraction or multiple of a therapeutic individual dose. An individual dose preferably contains the amount of active compound which is given in one administration and usually corresponds to a whole daily dose or a half, one-third or one-quarter of the daily dose. If only a fraction, such as a half or one-quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention contain from about 2 to 200 mg, advantageously from 10 to 100 mg and, in particular, from 20 to 60 mg of active compound.

In general, it is advantageous in human medicine to administer the active compound or compounds, when these are given orally, in a daily dose of from about 0.1 to about 30, preferably from 0.3 to 15 and, in particular, from 0.6 to 3 mg/kg of body weight, if appropriate in the form of several, preferably 1 to 3, individual administrations to achieve the desired results. An individual administration contains the active compound or compounds in amounts of from about 0.05 to about 10, preferably from 0.1 to 5 and, in particular, from 0.3 to 1 mg/kg of body weight.

Similar dosages are used in parenteral treatment, for example intravenous or intramuscular administration. From about 0.3 to 1 mg of active compound/kg of body weight is administered for this therapy.

For long-term medication, the pharmaceutical formulation is generally administered, for therapeutic purposes, at fixed points in time, such as 1 to 4 times daily, for example after each meal and/or in the evening. In acute cases, medication takes place at varying points in time. Under certain circumstances, it may be necessary to deviate from the mentioned dosages and, in particular, to do so in accordance with the nature, body weight and age of the patient being treated, the nature and severity of the illness, the frequency of administration, the nature of the formulation and of the mode of administration of the medicament, and the time or interval over which administration takes place. Thus, in some cases it may be sufficient to manage with less than the indicated amount of active compound, while such amount of active compound must be exceeded in other cases. The optimum dosage and method of administration of the active compounds required in each particular case are readily determined by the expert in accordance with his expert knowledge.

The pharmaceutical formulations ordinarily comprise one or more active compounds according to the invention and nontoxic, pharmaceutically-acceptable medicinal excipient. Excipients are used, e.g., as an admixture or diluent in solid, semi-solid or liquid form, or as a means of encasing, for example in the form of a capsule, a tablet coating, a sachet or some other container, for the therapeutically-active ingredient. An excipient serves, for example, as a promoter of the resorption of the medicament by the body, as a formulating auxiliary, as a sweetener, as a flavor correctant, as a colorant or as a preservative.

Examples of oral dosage forms are tablets, dragees, hard and soft capsules (for example, made of gelatin), dispersible powders, granules, aqueous and oily suspensions, emulsions or solutions.

Tablets contain, e.g., inert diluents, such as calcium carbonate, calcium phosphate, sodium phosphate or xylitol; granulating agents and dispersing agents, such as calcium phosphate or alginates; binders, such as starch, gelatin or gum acacia; and lubricants, such as aluminum or magnesium stearate, talc or silicone oil. The tablets are optionally provided with a coating, such as one which brings about delayed dissolution and resorption of the medicament in the gastrointestinal tract and hence, for example, better toleration, a protracted effect or a retarded effect. Gelatin capsules optionally contain the medicament mixed with a solid diluent, for example calcium carbonate or kaolin, or an oily diluent, for example paraffin oil.

Aqueous suspensions contain, e.g., suspending agents, such as sodium carboxymethylcellulose, methylcellulose, hydroxypropylcellulose, sodium alginate, polyvinylpyrrolidone, gum tragacanth or gum acacia; dispersing agents and wetting agents, such as polyoxyethylene stearate, heptadecaethyleneoxycetanol, polyoxyethylene sorbitol monooleate, polyoxyethylene sorbitan monooleate or lecithin; preservatives, such as methyl hydroxybenzoate or propyl hydroxybenzoate; flavoring agents; and sweeteners, such as saccharin or sodium cyclamate.

Oily suspensions contain, for example, paraffin oil, and thickeners, such as beeswax, hard paraffin or cetyl alcohol; and furthermore sweeteners, flavoring agents and antioxidants.

Water dispersible powders and granules contain the medicaments mixed, e.g., with dispersing agents, wetting agents and suspending agents, for example those previously mentioned, as well as sweeteners, flavoring agents and colorants.

Emulsions contain, for example, paraffin oil in addition to emulsifying agents, such as gum acacia, gum tragacanth, phosphatides, sorbitan monooleate or polyoxyethylene sorbitan monooleate, and sweeteners and flavoring agents.

For parenteral administration of the medicaments, sterile injectable aqueous suspensions, isotonic salt solutions or other solutions, which optionally contain dispersing agents or wetting agents and/or pharmacologically-acceptable diluents, for example propylene glycol or butylene glycol, are used.

The active compound or compounds is also optionally prepared in a micro-encapsulated form, if appropriate together with one or more of the noted excipients or additives.

In addition to the substituted oxiranecarboxylic acids according to the invention, in which the substituents have their previously-ascribed meanings, and/or their salts, the pharmaceutical formulations alternatively contain one or more pharmacologically-active ingredients from other groups of medicaments, such as antidiabetic agents (sulfonamides and sulfonylureas), for example carbutamide, tolbutamide, clorpropamide, glibenclamide, glibornuride, glisoxepide, gliquidone and glymidine, or hypolipidaemic agents, such as nicotinic acid and derivatives and salts thereof.

The invention also relates to a process for preparing substituted oxiranecarboxylic acids of formula I and salts of the acids, characterized by oxidizing substituted α-methylenecarboxylic acids of the formula

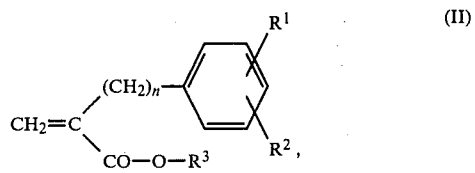

(II)

wherein $R^1$, $R^2$, $R^3$ and n have their previously-ascribed meanings, and optionally saponifying the resulting lower alkyl esters or optionally converting the resulting acids into salts or lower alkyl esters.

The oxidation of the α-methylenecarboxylic acids II is effected under known and well-established conditions for oxidation of carbon-carbon double bonds to obtain epoxides. Suitable oxidizing agents include peroxo compounds, such as hydrogen peroxide, peracetic acid, trifluoroperacetic acid, 3,5-dinitroperbenzoic acid and, preferably m-chloroperbenzoic acid. The reaction is appropriately carried out in inert solvent, for example an aromatic or chlorinated hydrocarbon, such as benzene, toluene, methylene chloride or chloroform. The reaction temperature is between 0° C. and the boiling point of the solvent, preferably between 20° and 70° C.

The saponification of lower alkyl esters is also effected conventionally. It is carried out, for example, with an aqueous or alcoholic (for example ethanolic) alkali-metal hydroxide (for example potassium hydroxide) solution at room temperature, optionally with the inclusion of an inert diluent, such as dioxane, tetrahydrofurane or toluene.

The conversion of acids of formula I ($R^3 = -H$) or of embodiments I*, I and I* into salts is effected, e.g., by direct alkaline hydrolysis of the acid derivatives I ($R^3$ = lower alkyl). That inorganic or organic base of which the salt is desired is used as the alkaline reactant. The salts are alternatively obtained by reacting the acids I ($R^3 = -H$) with the stoichiometric equivalent of the corresponding base, for example sodium hydroxide or sodium ethanolate, by converting readily-soluble salts into sparingly-soluble salts by double decomposition or by converting any salt into a pharmacologically-acceptable salt.

The conversion of oxiranecarboxylic acids of formula I ($R^3 = -H$) or of embodiments I*, I and I* into corresponding lower alkyl esters ($R^3$ = lower alkyl) is effected in a well-established manner. For example, they are esterified (a) with a lower alkanol in a reaction medium comprising strong acid, such as sulfuric acid or p-toluenesulfonic acid, or acid ion exchanger under conditions in which no decarboxylation takes place or (b) with dialkylsulfate or an alkyl halide in a reaction medium comprising diazabicycloundecene or diazabicyclononene in inert solvent, such as benzene, toluene or acetone.

The compounds of the general formula I are normally obtained in the form of racemic mixtures which, by means of known processes, are separated into the enantiomers. For example, the racemate is converted with an optically-active splitting agent into diastereoisomers which subsequently are separated by selective crystallization and converted into the appropriate optical isomers. Suitable optically-active splitting agents include, e.g., optically-active bases, such as l- and d-1-phenylethyl amine, cinchonidine or d-ephedrine, from which salts of the acids of formula I are prepared, or optically-active alcohols, such as borneol or menthol, from which esters of the acids of formula I are prepared. The racemic mixtures are also separated by chromatography via optically-active sorbing agents. Alternatively, the α-methylenecarboxylic acids II are primarily reacted with an optically-active splitting agent, e.g. borneol or menthol; the obtained products are subsequently oxidized to the mixtures of the diastereoisomers of the oxiranecarboxylic acid esters, from which the optical isomers of the acids I are obtained in a manner known to the expert.

α-Methylenecarboxylic acids of formula II, wherein $R^1$, $R^2$, $R^3$ and n have their respective meanings for embodiments I*, I and I*, are employed for preparing the substituted oxiranecarboxylic acids of embodiments I*, I and I*.

The α-methylenecarboxylic acids of formula II are known or are prepared by conventional methods from known starting materials. They are valuable intermediate products for the synthesis of the oxiranecarboxylic acids I, I*, I and I*. Moreover, the α-methylenecarboxylic acids II (in which $R^1$ denotes a chlorine atom and $R^2$, $R^3$ and n have the meanings indicated for embodiment I) and the α-methylenecarboxylic acids II* (in which $R^1$, $R^2$, $R^3$ and n have the meanings indicated for embodiment I*) also have hypoglycemic activity. 5-(3-Chlorophenyl)-α-methylenevaleric acid ethyl ester, α-methylene-7-phenylheptanoic acid, 7-(4-chlorophenyl)-α-methyleneheptanoic acid and, in particular, 5-(4-chlorophenyl)-α-methylenevaleric acid ethyl ester are exemplary. Compounds II (in which $R^1$ denotes a chlorine atom) and II* are useful both as intermediates and as medicaments. The medicaments are formulated in a known manner by previously-described methods.

The α-methylenecarboxylic acids II are prepared, for example, by a process analogous to that of H. Stetter and H. Kuhlmann [Synthesis 1979, 29] by reacting a malonic acid half-ester of the formula

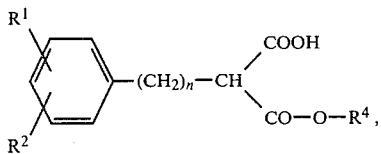

(III)

wherein $R^1$, $R^2$ and n have their previously-indicated meanings and $R^4$ denotes a lower alkyl group, with formaldehyde in a reaction medium comprising pyridine and secondary amine, preferably piperidine, and optionally saponifying the lower alkyl esters obtained.

Alternatively, the α-methylenecarboxylic acids II are prepared by methods analogous to those described by Ph. E. Pfeffer et al. [J. Org. Chem., 37 (1972) 1,256] and W. S. Wadsworth, junior, and W. D. Emmons [J. Am. Chem. Soc., 83 (1961) 1,733]. 5-Phenyl-α-methylenevaleric acid and 3-phenyl-α-methylenepropionic acid are considered by C. Mannich and E. Ganz [Ber. Dtsch. Chem. Ges., 55 (1922) 3,486]. 3-Phenyl-α-methylenepropionic acid ethyl ester is considered by Y. Ueno et al. [Tetrahedron Letters, 1978, 3,753] and 4-phenyl-α-methylenebutyric acid ethyl ester is considered by F. Hahne and F. Zymalkowski [Arch. Pharm., 312 (1979) 472].

The malonic acid half-esters III are prepared by methods with which those skilled in the art are familiar, for example by reacting dialkyl malonates IV with phenylalkyl compounds V and partially hydrolyzing the resulting malonic acid diesters VI, according to the following reaction scheme:

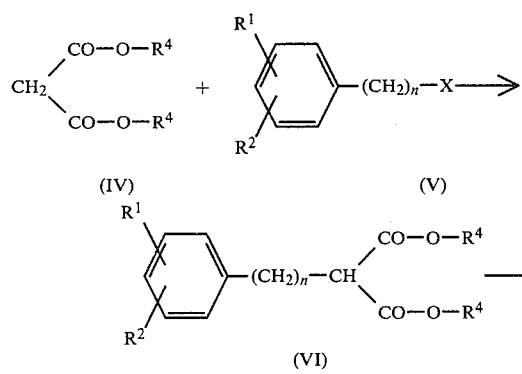

wherein
$R^1$, $R^2$, $R^4$ and n have their previously-noted meanings and
X denotes a leaving group, for example a chlorine or bromine atom or a mesyloxy or p-toluenesulfonyloxy group.

Appropriate starting compounds III*, III or III*; IV*, IV or IV*; V*, V or V*; and VI*, VI or VI* (in which $R^1$, $R^2$ and n have the meanings corresponding to those for embodiments I*, I and I*, respectively, and $R^{4*}$ denotes a lower alkyl group, $R^{4}$ and $R^{4*}$, respectively, denote a methyl or ethyl group, and X*, X and X*, respectively, denote a chlorine or bromine atom or a mesyloxy- or p-toluenesulfonyloxy group) are employed for the preparation of α-methylenecarboxylic acids II*, II and II*.

The following Examples, wherein b.p. denotes boiling point and m.p. denotes melting point, illustrate the invention without limiting it. The temperature data are in °C.

EXAMPLE 1

2-(3-Phenylpropyl)oxirane-2-carboxylic acid ethyl ester (a) 2-(3-Phenylpropyl)oxirane-2-carboxylic acid ethyl ester 10 g of 5-phenyl-2-methylenevaleric acid ethyl ester and 18.3 g of m-chloroperbenzoic acid (85% pure) are boiled under reflux in 180 ml of methylene chloride for 40 hours. The mixture is allowed to cool; the m-chloroperbenzoic acid (which has separated out) is filtered off; the filtrate is concentrated; the residue is taken up in 40 ml of acetone; 20 ml of a saturated sodium carbonate solution are added, and the mixture is stirred at 0° C. for 1 hour. It is then diluted with 100 ml of water and extracted 3 times with 50 ml of methylene chloride each time; the organic phase is concentrated, and the residue is distilled. 8.3 g of the liquid title compound (b.p. 115° under 0.03 mm Hg) are obtained.

(b) 5-Phenyl-2-methylenevaleric acid ethyl ester 50 g of 3-phenylpropylmalonic acid monoethyl ester, 7.5 g of paraformaldehyde, 37.5 ml of pyridine and 2.5 ml of piperidine are stirred together at 50° C. for 5 hours. After cooling, 350 ml of water are added to the reaction mixture, and the mixture is then extracted 3 times with 150 ml of hexane each time. After washing with 1 N hydrochloric acid, water and sodium bicarbonate solution, the organic phase is concentrated and distilled. 5-Phenyl-2-methylenevaleric acid ethyl ester is obtained as a colorless liquid of b.p. 78° to 79° C. under 0.02 mm Hg.

Alternatively, 5-phenyl-2-methylenevaleric acid ethyl ester is obtained by esterifying 5-phenyl-2-methylenevaleric acid with ethanol in the presence of p-toluenesulfonic acid.

EXAMPLE 2

2-(3-Phenylpropyl)oxirane-2-carboxylic acid 6.0 g of 2-(3-phenylpropyl)oxirane-2-carboxylic acid ethyl ester, 26 ml of 1 N sodium hydroxide solution and 60 ml of ethanol are stirred at room temperature for 1 hour; 13 ml of 2 N hydrochloric acid are added to the solution (while cooling with ice), and the mixture is then concentrated to one third of its volume in vacuo. 50 ml of water are added to the thus-concentrated solution, and the resulting mixture is extracted 3 times with 50 ml of diethyl ether each time. After drying the organic phase over sodium sulfate and evaporating off the solvent, 4.3 g of a viscous oil are obtained.

Alternatively, the compound is obtained as follows: a solution of trifluoroperacetic acid (prepared from 1.8 ml of 85% strength hydrogen peroxide, 17 g of trifluoroacetic anhydride and 15 ml of methylene chloride) is added dropwise to a boiling mixture of 9.5 g of 5-phenyl-2-methylenevaleric acid and 28 g of disodium hydrogen phosphate in 50 ml of methylene chloride. The mixture is boiled under reflux for a further 30 minutes; 150 ml of ice-water are added; *the organic phase is separated off and, after drying over sodium sulfate, is concentrated. The title compound remains as a viscous oil.

*the pH is adjusted to 2 with hydrochloric acid;

EXAMPLE 3

2-(4-Phenylbutyl)oxirane-2-carboxylic acid ethyl ester (a) 2-(4-Phenylbutyl)oxirane-2-carboxylic acid ethyl ester 7.6 g of the title compound (b.p. 105° C. under 0.005 mm Hg) are obtained from 12 g of 6-phenyl-2-methylenehexanoic acid ethyl ester and 26.5 g of m-chloroperbenzoic acid in 160 ml of methylene chloride by the procedure described in Example 1a.

(b) 6-Phenyl-2-methylenehexanoic acid ethyl ester 49 g of 6-phenyl-2-methylenehexanoic acid ethyl ester (b.p. 120° to 125° C. under 0.005 mm Hg) are obtained from 72 g of 4-phenylbutylmalonic acid monoethyl ester, 11.3 g of paraformaldehyde, 51.3 ml of pyridine and 3.4 ml of piperidine by the procedure described in Example 1b.

(c) 4-Phenylbutylmalonic acid monoethyl ester

A solution of 17.8 g of potassium hydroxide in 200 ml of ethanol is added dropwise to 91 g of 4-phenylbutylmalonic acid diethyl ester in 200 ml of ethanol at room temperature (20° C.). The mixture is stirred for 24 hours and substantially concentrated in vacuo; the residue is taken up in 500 ml of water, and the aqueous mixture is extracted twice with 100 ml of diethyl ether each time. The aqueous phase is acidified with concentrated hydrochloric acid (while cooling with ice) and extracted 3 times with 200 ml of diethyl ether each time; after drying over sodium sulfate, the organic phase is concentrated. 72.8 g of a viscous oil remain.

EXAMPLE 4

2-[3-(2-Chlorophenyl)propyl]oxirane-2-carboxylic acid ethyl ester (a) 2-[3-(2-Chlorophenylpropyl]oxirane-2-carboxylic acid ethyl ester 5.0 g of the title compound (b.p. 110° to 113° C. under 0.007 mm Hg) are obtained from 14 g of 5-(2-chlorophenyl)-2-methylenevaleric acid ethyl ester and 22.5 g of m-chloroperbenzoic acid in 170 ml of methylene chloride by the procedure described in Example 1a.

(b) 5-(2-Chlorophenyl)-2-methylenevaleric acid ethyl ester 53.3 g of 5-(2-chlorophenyl)-2-methylenevaleric acid ethyl ester (b.p. 95° to 98° C. under 0.005 mm Hg) are obtained from 71 g of 3-(2-chlorophenyl)acid monoethyl ester, 10.42 g of paraformaldehyde, 47 ml of pyridine and 3.1 ml of piperidine by the procedure described in Example 1b.

(c) 3-(2-Chlorophenyl)propylmalonic acid monoethyl ester 71.8 g of 3-(2-chlorophenyl)propylmalonic acid monoethyl ester are obtained as a viscous oil from 92 g of 3-(2-chlorophenyl)propylmalonic acid diethyl ester and 16.8 g of potassium hydroxide in 400 ml of ethanol by the procedure described in Example 3c.

EXAMPLE 5

2-[3-(3-Chlorophenyl)propyl]oxirane-2-carboxylic acid ethyl ester (a) 2-[3-(3-Chlorophenyl)propyl]oxirane-2-carboxylic acid ethyl ester 10.8 g of the title compound (b.p. 135° to 138° C. under 0.005 mm Hg) are obtained from 14 g of 5-(3-chlorophenyl)-2-methylenevaleric acid ethyl ester and 22.5 g of m-chloroperbenzoic acid in 170 ml of methylene chloride by the procedure described in Example 1a.

(b) 5-(3-Chlorophenyl)-2-methylenevaleric acid ethyl ester 35.75 g of 5-(3-chlorophenyl)-2-methylenevaleric acid ethyl ester (b.p. 105° to 110° C. under 0.005 mm Hg) are obtained from 57 g of 3-(3-chlorophenyl)-propylmalonic acid ethyl ester, 8.36 g of paraformaldehyde, 37.7 ml of pyridine and 2.5 ml of piperidine by the procedure described in Example 1b.

(c) 3-(3-Chlorophenyl)propylmalonic acid ethyl ester 57.7 g of 3-(3-chlorophenyl)propylmalonic acid ethyl ester are obtained as a viscous oil from 74 g of 3-(3-chlorophenyl)propylmalonic acid diethyl ester and 13.5 g of potassium hydroxide in 200 ml of ethanol by the procedure described in Example 3c.

(d) 3-(3-Chlorophenyl)propylmalonic acid diethyl ester 91.3 g of malonic acid diethyl ester are added dropwise, at 50° C., to a sodium ethylate solution freshly prepared from 13.11 g of sodium and 650 ml of ethanol. The mixture is kept at that temperature for 2.5 hours, and 185 g of p-toluenesulfonic acid [3-(3-chlorophenyl)-propyl] ester are then added dropwise. When the addition is complete, the obtained mixture is stirred at 50° C. for 6 hours; 800 ml of water are then added, and the mixture is extracted 3 times with a total of 1 liter of diethyl ether. The combined organic phases are dried over sodium sulfate; the solvent is evaporated off, and the residue is distilled. 74.2 g of 3-(3-chlorophenyl)-propylmalonic acid diethyl ester (b.p. 145° to 152° C. under 0.01 mm Hg) are obtained.

(e) p-Toluenesulfonic acid [3-(3-chlorophenyl)propyl] ester 86 ml of pyridine are added dropwise to 90 g of 3-(3-chlorophenyl)propan-1-ol and 124 g of p-toluenesulfonic acid chloride in 300 ml of chloroform at 0° C. When the addition is complete, the mixture is stirred at room temperature for 3 hours, and the solution is poured into a mixture of 400 ml of water and 120 ml of concentrated hydrochloric acid. The organic phase is separated off, washed 3 times with water, dried over sodium sulfate and concentrated to a viscous oil in vacuo.

EXAMPLE 6

2-[3-(4-Chlorophenyl)propyl]oxirane-2-carboxylic acid ethyl ester (a) 2-[3-(4-Chlorophenyl)propyl]oxirane-2-carboxylic acid ethyl ester 4.3 g of the title compound (b.p. 110° C. under 0.005 mm Hg) are obtained from 10.0 g 5-(4-chlorophenyl)-2-methylenevaleric acid ethyl ester and 20.3 g of m-chloroperbenzoic acid in 150 ml of methylene chloride by the procedure described in Example 1a.

(b) 5-(4-Chlorophenyl)-2-methylenevaleric acid ethyl ester 58.8 g of 5-(4-chlorophenyl)-2-methylenevaleric acid ethyl ester (b.p. 120° to 123° C. under 0.05 mm Hg) are obtained from 91.7 g of 3-(4-chlorophenyl)propylmalonic acid ethyl ester, 14.5 g of paraformaldehyde, 73.1 ml of pyridine and 4.8 ml of piperidine by the procedure described in Example 1b.

(c) 3-(4-Chlorophenyl)propylmalonic acid ethyl ester 92.2 g of 3-(4-chlorophenyl)propylmalonic acid ethyl ester are obtained as a viscous oil from 125.15 g of 3-(4-chlorophenyl)propylmalonic acid diethyl ester and 25.5 g of potassium hydroxide in 500 ml of ethanol by the procedure described in Example 3c.

(d) 3-(4-Chlorophenyl)propylmalonic acid diethyl ester 105.6 g of 3-(4-chlorophenyl)propylmalonic acid diethyl ester (b.p. 145° to 155° C. under 0.01 mm Hg) are obtained from 220 g of p-toluenesulfonic acid [3-(4-chlorophenyl)propyl] ester, 108.5 g of malonic acid diethyl ester and a solution of 15.6 g of sodium in 750 ml of ethanol by the procedure described in Example 5d.

(e) p-Toluenesulfonic acid [3-(4-chlorophenyl)propyl] ester 285 g of p-toluenesulfonic acid [3-(4-chlorophenyl)propyl] ester are obtained as a viscous, yellowish oil from 150 g of 3-(4-chlorophenyl)propan-1-ol, 206.6 g of p-toluenesulfonic acid chloride and 135 ml of pyridine in 300 ml of chloroform by the procedure described in Example 5e.

EXAMPLE 7

2-[3-(4-Methoxyphenyl)propyl]oxirane-2-carboxylic acid ethyl ester (a) 2-[3-(4-Methoxyphenyl)propyl]oxirane-2-carboxylic acid ethyl ester 5.8 g of the title compound (b.p. 120° to 125° C. under 0.005 mm Hg) are obtained from 10 g of 5-(4-methoxyphenyl)-2-methylenevaleric acid ethyl ester and 20 g of m-chloroperbenzoic acid in 150 ml of methylene chloride by the procedure described in Example 1a.

(b) 5-(4-Methoxyphenyl)-2-methylenevaleric acid ethyl ester 31.5 g of 5-(4-methoxyphenyl)-2-methylenevaleric acid ethyl ester (b.p. 134° to 135° C. under 0.05 mm Hg) are obtained from 50 g of 3-(4-methoxyphenyl)propylmalonic acid ethyl ester, 33.7 ml of pyridine, 2.2 ml of piperidine and 7.4 g of paraformaldehyde by the procedure described in Example 1b.

(c) 3-(4-Methoxyphenyl)propylmalonic acid ethyl ester 50.3 g of 3-(4-methoxyphenyl)propylmalonic acid ethyl ester are obtained as a viscous oil from 63 g of 3-(4-methoxyphenyl)propylmalonic acid diethyl ester and 12.7 g of potassium hydroxide in 250 ml of ethanol by the procedure described in Example 3c.

EXAMPLE 8

2-[3-(3-Trifluoromethylphenyl)propyl]oxirane-2-carboxylic acid ethyl ester (a) 2-[3-(3-Trifluoromethylphenyl)propyl]oxirane-2-carboxylic acid ethyl ester 8.5 g of the title compound (b.p. 110° C. under 0.07 mm Hg) are obtained from 15 g of 2-methylene-5-(3-trifluoromethylphenyl)valeric acid ethyl ester and 21.27 g of m-chloroperbenzoic acid in 150 ml of methylene chloride by the procedure described in Example 1a.

(b) 2-Methylene-5-(3-trifluoromethylphenyl)valeric acid ethyl ester 19.53 g of 2-methylene-5-(3-trifluoromethylphenyl)valeric acid ethyl ester (b.p. 98° to 110° C. under 0.07 mm Hg) are obtained from 35.4 g of 3-(3-trifluoromethylphenyl)propylmalonic acid ethyl ester, 4.24 g of paraformaldehyde, 19.2 ml of pyridine and 1.27 ml of piperidine by the procedure described in Example 1b.

(c) 3-(3-Trifluoromethylphenyl)propylmalonic acid ethyl ester 36.2 g of 3-(3-trifluoromethylphenyl)propylmalonic acid ethyl ester are obtained as a viscous oil from 45.3 g of 3-(3-trifluoromethylphenyl)propylmalonic acid diethyl ester and 7.5 g of potassium hydroxide in 260 ml of ethanol by the procedure described in Example 3c.

(d) 3-(3-Trifluoromethylphenyl)propylmalonic acid diethyl ester 50.6 g of 3-(3-trifluoromethylphenyl)propylmalonic acid diethyl ester (b.p. 118° to 120° C. under 0.07 mm Hg) are obtained from 125 g of p-toluenesulfonic acid [3-(3-trifluoromethylphenyl)propyl] ester, 58.1 g of malonic acid diethyl ester and a solution of 8.5 g of sodium in 400 ml of ethanol by the procedure described in Example 5d.

(e) p-Toluenesulfonic acid [3-(3-trifluoromethylphenyl)propyl] ester 125 g of p-toluenesulfonic acid [3-(3-trifluoromethylphenyl)propyl] ester are obtained as a yellow oil from 71.5 g of 3-(3-trifluoromethylphenyl)propan-1-ol, 83 g of p-toluenesulfonic acid chloride and 54 ml of pyridine in 160 ml of chloroform by the procedure described in Example 5e.

(f) 3-(3-Trifluoromethylphenyl)propan-1-ol

A solution of 57 g of oxirane in 120 ml of diethyl ether is added dropwise (at 0° to 10° C.) to a Grignard solution prepared from 14.8 g of magnesium and 100 g of 3-(chloromethyl)benzotrifluoride in 450 ml of diethyl ether. The mixture is subsequently stirred at room temperature for 1 hour, and 300 ml of 10% strength sulfuric acid are then added, while cooling with ice. The organic phase is collected and extracted twice more with diethyl ether, and the combined organic phases are dried over magnesium sulfate and distilled. 76.7 g of 3-(3-trifluoromethylphenyl)propan-1-ol (b.p. 85° to 95° C. under 0.02 mm Hg) are thus obtained.

EXAMPLE 9

2-[3-(4-Methylphenyl)propyl]oxirane-2-carboxylic acid ethyl ester (a) 2-[3-(4-Methylphenyl)propyl]oxirane-2-carboxylic acid ethyl ester 6.8 g of the title compound (b.p. 110° to 115° C. under 0.005 mm Hg) are obtained from 10 g of 5-(4-methylphenyl)-2-methylenevaleric acid ethyl ester and 11.8 g of 3,5-dinitroperbenzoic acid in 100 ml of methylene chloride by the procedure described in Example 1a.

(b) 5-(4-Methylphenyl)-2-methylenevaleric acid ethyl ester 46.5 g of 5-(4-methylphenyl)-2-methylenevaleric acid ethyl ester (b.p. 120° to 128° C. under 0.008 mm Hg) are obtained from 72 g of 3-(4-methylphenyl)propylmalonic acid ethyl ester, 11.3 g of paraformaldehyde, 51 ml of pyridine and 3.4 ml of piperidine by the procedure described in Example 1b.

(c) 3-(4-Methylphenyl)propylmalonic acid ethyl ester 73.2 g of 3-(4-methylphenyl)propylmalonic acid ethyl ester are obtained from 90 g of 3-(4-methylphenyl)propylmalonic acid diethyl ester and 17.6 g of potassium hydroxide by the procedure described in Example 3c.

EXAMPLE 10

2-(5-Phenylpentyl)oxirane-2-carboxylic acid ethyl ester (a) 2-(5-Phenylpentyl)oxirane-2-carboxylic acid ethyl ester 7.9 g of the title compound (b.p. 115° to 120° C. under 0.005 mm Hg) are obtained from 13 g of 2-methylene-7-phenylheptanoic acid ethyl ester and 21.4 g of m- chloroperbenzoic acid in 160 ml of methylene chloride by the procedure described in Example 1a.

(b) 2-Methylene-7-phenylheptanoic acid ethyl ester 20.65 g of 2-methylene-7-phenylheptanoic acid ethyl ester are obtained as an oil (b.p. 122° to 125° C. under 0.07 mm Hg) from 44 g of 5-phenylpentylmalonic acid ethyl ester, 6.6 g of paraformaldehyde, 30 ml of pyridine and 2 ml of piperidine by the procedure described in Example 1b.

(c) Phenylpentylmalonic acid ethyl ester 44.8 of 5-phenylpentylmalonic acid ethyl ester are obtained as a viscous oil from 60 g of 5-phenylpentylmalonic acid diethyl ester and 11.16 g of potassium hydroxide in 250 ml of ethanol by the procedure described in Example 3c.

(d) 5-Phenylpentylmalonic acid diethyl ester 66.8 g of 5-phenylpentylmalonic acid diethyl ester are obtained as an oil (b.p. 142° to 148° C. under 0.02 mm Hg) from 80.8 g of 1-bromo-5-phenylpentane, 64.1 g of malonic acid diethyl ester and a solution of 8.2 g of sodium in 400 ml of ethanol by the procedure described in Example 5d.

EXAMPLE 11

2-[5-(4-Chlorophenyl)pentyl]oxirane-2-carboxylic acid ethyl ester (a) 2-[5-(4-Chlorophenyl)pentyl]oxirane-2-carboxylic acid ethyl ester 8.8 g of the title compound (b.p. 135° to 140° C. under 0.005 mm Hg) are obtained from 15 g of 7-(4-chlorophenyl)-2-methyleneheptanoic acid ethyl ester and 23 g of m-chloroperbenzoic acid in 180 ml of methylene chloride by the procedure described in Example 1a.

(b) 7-(4-Chlorophenyl)-2-methyleneheptanoic acid ethyl ester 15.5 g of 7-(4-chlorophenyl)-2-methyleneheptanoic acid ethyl ester (b.p. 140° to 145° C. under 0.008 mm Hg) are obtained from 25 g of 5-(4-chlorophenyl)pentylmalonic acid ethyl ester, 3.8 g of paraformaldehyde, 16 ml of pyridine and 1 ml of piperidine by the procedure described in Example 1b.

(c) 5-(4-Chlorophenyl)pentylmalonic acid ethyl ester 26.5 g of 5-(4-chlorophenyl)pentylmalonic acid ethyl ester are obtained as a viscous oil from 34 g of 5-(4-chlorophenyl)pentylmalonic acid diethyl ester and 5.7 g of potassium hydroxide in 150 ml of ethanol by the procedure described in Example 3c.

(d) 5-(4-Chlorophenyl)pentylmalonic acid diethyl ester 35.5 g of 5-(4-chlorophenyl)pentylmalonic acid diethyl ester are obtained as an oil from 70.5 g of p-toluenesulfonic acid [5-(4-chlorophenyl)pentyl] ester, 32 g of malonic acid diethyl ester and a solution of 4.6 g of sodium in 250 ml of ethanol by the procedure described in Example 5d.

EXAMPLE 12

2-[3-(4-Chlorophenyl)propyl]oxirane-2-carboxylic acid

The title compound is obtained as a viscous oil from 1.0 g of 2-[3-(4-chlorophenyl)propyl]oxirane-2-carboxylic acid ethyl ester and 3.72 ml of 1 N sodium hydroxide solution by the procedure described in Example 2.

EXAMPLE 13

2-(3-Phenylpropyl)oxirane-2-carboxylic acid methyl ester

The title compound is obtained as a colorless oil (b.p. 75° to 80° C. under 0.01 mm Hg) analogously to Example 3a.

The starting compound 5-phenyl-2-methylenevaleric acid methyl ester is obtained from 3-phenylpropylmalonic acid dimethyl ester analogously to Example 3b and 3c.

EXAMPLE 14

Sodium 2-(3-phenylpropyl)oxirane-2-carboxylate 5 g of 2-(3-phenylpropyl)oxirane-2-carboxylic acid is dissolved in the equivalent amount of 1 N sodium hydroxide solution, and the resulting aqueous solution is washed once with diethyl ether and evaporated to dryness. The glassy residue, which is dried at 20° C. in vacuo, consists of the pure sodium salt.

EXAMPLE 15

2-Benzyloxirane-2-carboxylic acid ethyl ester 7.6 g of the title compound (b.p. 79° to 80° C. under 0.003 mm Hg) are obtained from 15.0 g of 2-methylene-3-phenylpropionic acid ethyl ester and 32.0 g of m-chloroperbenzoic acid in 300 ml of methylene chloride by the procedure described in Example 1a.

EXAMPLE 16

2-(2-Phenylmethyl)oxirane-2-carboxylic acid ethyl ester 9 g of 4-phenyl-2-methylenebutyric acid ethyl ester and 22.3 g of m-chloroperbenzoic acid (85% pure) are boiled under reflux in 150 ml of methylene chloride for 24 hours. The mixture is allowed to cool; the m-chlorobenzoic acid (which has separated out) is filtered off; the filtrate is concentrated; the resulting residue is taken up in 30 ml of acetone; 15 ml of a saturated sodium carbonate solution are then added, and the obtained mixture is stirred at 0° C. for 1 hour. It is diluted with 100 ml of water and extracted 3 times with 50 ml of methylene chloride each time. The organic phase is concentrated, and the oily residue is distilled. 7.3 g of the title compound (b.p. 110° to 112° C. under 0.01 mm Hg) are thus obtained.

EXAMPLE 17

Sodium 2-[3-(3-chlorophenyl)propyl]oxirane-2-carboxylate 2.7 g of 2-[3-(3-chlorophenyl)propyl]oxirane-2-carboxylic acid ethyl ester are stirred with 10 ml of 1 N sodium hydroxide solution and 10 ml of ethanol at room temperature for 1 hour. The mixture is concentrated in vacuo, after which the title compound remains as a colorless glassy powder.

EXAMPLE 18

2-[3-(2-Chlorophenyl)propyl]oxirane-2-carboxylic acid ethyl ester

A mixture of 104 ml of 15% strength butyl-lithium (in hexane), 19 g of diisopropylamine and 400 ml of tetrahydrofuran is stirred together at −78°; 39 g of 5-(2-chlorophenyl)-2-acetylvaleric acid ethyl ester [prepared from 3-(2-chlorophenyl)propyltosylate and ethyl acetoacetate] are added dropwise to the resulting admixture. The mixture thus obtained is stirred for a further 20 minutes. After removing the cooling bath, 19.4 g of paraformaldehyde (anhydrous) are added in portions to the mixture. After stirring the mixture for 1 hour, it is heated under reflux for 5 hours and left to stand overnight. The solid constituents are filtered off, and the filtrate is concentrated in a rotary evaporator. 500 ml of saturated sodium bicarbonate solution are added to the residue, and the mixture is stirred for 30 minutes. Extraction with methylene chloride and evaporation of the solvent yield (after purification by distillation) 14 g of 5-(2-chlorophenyl)-2-methylenevaleric acid ethyl ester of b.p. 95° to 98° C. under 0.005 mm Hg. The title compound is obtained analogously to Example 4a by oxidation.

EXAMPLE 19

Sodium 2-[3-(4-chlorophenyl)propyl]oxirane-2-carboxylate

A solution of 4.2 g of 2-[3-(4-chlorophenyl)propyl]oxirane 2-carboxylic acid ethyl ester is added dropwise to a solution of 0.36 g of sodium in 15 ml of ethanol, 0.28 g of water is then added and the mixture is stirred at room temperature for 1 hour. The precipitate which has separated out is filtered off, washed with diethyl ether and recrystallized once from ethanol/diethyl ether. 2.0 g of the title compound of m.p. 160° to 167° C. are obtained.

EXAMPLE 20

Sodium 2-[3-(3-trifluoromethylphenyl)propyl]oxirane-2-carboxylate

A solution of 28 g of 2-[3-(3-trifluoromethylphenyl)propyl]oxirane-2-carboxylic acid ethyl ester in 50 ml of tetrahydrofuran is added dropwise to a solution of 92.6 ml of 1 N sodium hydroxide solution and 50 ml of tetrahydrofuran at room temperature. After a clear solution has formed, the solution is concentrated to a viscous mass in vacuo. The mass is dissolved in 70 ml of tetrahydrofuran, the small amount of undissolved material is filtered off, and 200 ml of methylene chloride are added dropwise to the clear filtrate. The voluminous precipitate is filtered off and stirred again with 200 ml of diethyl ether, the mixture is filtered and the solid product is dried over calcium chloride. The title compound of m.p. 64° to 70° C., which contains 2 mols of water of crystallization, is converted into the form containing no water of crystallization, of m.p. >170° C., when dried over phosphorus pentoxide in vacuo (yield: 22.8 g).

EXAMPLE 21

Sodium 2-(5-phenylpentyl)oxirane-2-carboxylate

A mixture of 166 ml of 1 N sodium hydroxide solution and 90 ml of tetrahydrofuran is added dropwise to a solution of 43.6 g of 2-(5-phenylpentyl)oxirane 2-carboxylic acid ethyl ester in 90 ml of tetrahydrofuran. When the addition has ended, the mixture is stirred for about 45 minutes, until a clear solution has formed. 1.6 l of acetone are now added dropwise in the course of 3 hours, a crystalline precipitate, which is filtered off and washed with acetone, separating out. The product is recrystallized from water to give 42.9 g of the title compound as the dihydrate of m.p. 82° to 86° C.

EXAMPLE 22

Sodium 2-[5-(4-chlorophenyl)pentyl]oxirane-2-carboxylate

A mixture of 8.05 g of 2-[5-(4-chlorophenyl)pentyl]oxirane 2-carboxylic acid ethyl ester, 27 ml of tetrahydrofuran and 27 ml of 1 N sodium hydroxide solution is stirred for about 1 hour until a clear solution has formed. The solution is concentrated and the colorless residue is recrystallized from ethanol/diethyl ether. 6.5 g of the title compound of m.p. 136° to 142° C. are obtained.

EXAMPLE 23

Sodium 2-[3-(4-methylphenyl)propyl]oxirane-2-carboxylate 2.7 g of the title compound of m.p. >250° C. (from methanol/diethyl ether) are obtained from a solution of 0.7 g of sodium in 70 ml of ethanol, 0.5 ml of water and 7.0 g of 2-[3-(4-methylphenyl)propyl]oxirane 2-carboxylic acid ethyl ester by the procedure described in Example 19.

EXAMPLE 24

2-[3-(4-Fluorophenyl)propyl]oxirane-2-carboxylic acid ethyl ester (a) 2-[3-(4-Fluorophenyl)propyl]oxirane-2-carboxylic acid ethyl ester 23.8 g of the title compound of b.p. 115° to 117° C. under 0.02 mm Hg are obtained from 25.4 g of 5-(4-fluorophenyl)-2-methylenevaleric acid ethyl ester and 32.2 g of m-chloroperbenzoic acid in 330 ml of methylene chloride by the procedure described in Example 1a.

(b) 5-(4-Fluorophenyl)-2-methylenevaleric acid ethyl ester 25.7 g of 5-(4-Fluorophenyl)-2-methylenevaleric acid ethyl ester of b.p. 84° to 86° C. under 0.01 mm Hg are obtained from 43.5 g of 3-(4-fluorophenyl)propylmalonic acid ethyl ester, 5.1 g of paraformaldehyde, 50 ml of pyridine and 1.6 ml of piperidine by the procedure described in Example 1b.

(c) 3-(4-Fluorophenyl)propylmalonic acid ethyl ester 43.5 g of 3-(4-fluorophenyl)propylmalonic acid ethyl ester are obtained as a yellowish oil from 80 g of 3-(4-fluorophenyl)propylmalonic acid diethyl ester and 16.6 g of potassium hydroxide in 170 ml of ethanol by the procedure described in Example 3c.

(d) 3-(Fluorophenyl)propylmalonic acid diethyl ester 80 g of 3-(4-fluorophenyl)propylmalonic acid diethyl ester are obtained as a yellowish oil from 83 g of p-toluenesulfonic acid 3-(4-fluorophenyl)propyl ester, 43.3 g of malonic acid diethyl ester and a solution of 6.5 g of sodium in 400 ml of ethanol by the procedure described in Example 5d.

(e) p-Toluenesulfonic acid 3-(4-fluorophenyl)propyl ester 83 g of p-toluenesulfonic acid 3-(4-fluorophenyl)propyl ester are obtained as a yellowish oil from 39.7 g of 3-(4-fluorophenyl)propan-1-ol, 54 g of p-toluenesulfonic acid chloride and 83 ml of pyridine in 200 ml of toluene, after stirring at room temperature for 40 hours, by the procedure described in Example 5e.

(f) 3-(4-Fluorophenyl)propan-1-ol

A solution of 43.6 g of 3-(4-fluorophenyl)propionic acid in 300 ml of tetrahydrofuran is added dropwise to a suspension of 19.7 g of lithium aluminum hydride in 300 ml of tetrahydrofuran at a reaction temperature of about 45° C., while stirring. When the addition is complete, the above temperature is maintained for a further 2.5 hours and 80 ml of water and 20 ml of 4 N sodium hydroxide solution are then successively added dropwise. The precipitate is filtered off and rinsed several times with diethyl ether and the combined solutions are dried over sodium sulfate and concentrated. 39.7 g of 3-(4-fluorophenyl)propan-1-ol remain as an almost colourless oil.

(g) 3-(4-Fluorophenyl)propionic acid 91.6 g of malonic acid diethyl ester are added dropwise to a solution of 12.6 g of sodium in 300 ml of ethanol, the mixture is subsequently stirred for a further 15 minutes and 98.3 g of 4-fluorobenzyl bromide are then added dropwise. The mixture is subsequently boiled for a further 3 hours under reflux, most of the solvent is distilled off, the residue is taken up in ice-water (800 ml) and methylene chloride (600 ml) and the mixture is shaken thoroughly. The organic phase is collected and concentrated and the oil which remains (4-fluorobenzyl-malonic acid diethyl ester) (137.6 g) is stirred with a solution of 133 g of potassium hydroxide in 780 ml of methanol for 12 hours. The mixture is substantially concentrated in vacuo, the residue is dissolved in water/diethyl ether, the solution is shaken thoroughly, the organic phase is separated off and the aqueous phase is acidified with 10 N sulfuric acid, while cooling with ice. The mixture is extracted with methylene chloride, the organic phase is concentrated and the oily residue is stirred with petroleum ether/ethyl acetate (3:1), whereupon 53.6 g of 4-fluorobenzylmalonic acid crystallize out (m.p. 134° to 136° C.).

The 4-fluorobenzylmalonic acid is heated to 170° to 175° for 1.5 hours. After cooling, the reaction product is stirred with a little diethyl ether. 41.6 g of 3-(4-fluorophenyl)propionic acid of m.p. 85° to 88° [from ethyl acetate/petroleum ether (1:4)] thereby crystallize out.

EXAMPLE 25

2-(6-Phenylhexyl)oxirane-2-carboxylic acid ethyl ester (a) 2-(6-Phenylhexyl)oxirane-2-carboxylic acid ethyl ester 2.1 g of the title compound are obtained as a colourless oil, which is purified by chromatography on a silica gel column [eluant: petroleum ether/ethyl acetate (95:5)], from 4 g of 2-methylene-8-phenyloctanoic acid ethyl ester and 5.4 g of m-chloroperbenzoic acid in 150 ml of methylene chloride by the procedure described in Example 1a.

(b) 2-Methylene-8-phenyloctanoic acid ethyl ester 4.0 g of 2-methylene-8-phenyloctanoic acid ethyl ester are obtained as a colourless oil, which is purified over a silica gel column (eluant: methylene chloride), from 7 g of 6-phenylhexylmalonic acid ethyl ester, 0.8 g of paraformaldehyde, 10 ml of pyridine and 0.5 ml of piperidine by the procedure described in Example 1b.

(c) 6-Phenylhexylmalonic acid ethyl ester 14.5 g of 6-phenylhexylmalonic acid ethyl ester are obtained as a viscous oil from 20 g of 6-phenylhexylmalonic acid diethyl ester and potassium hydroxide by the procedure described in Example 3c.

(d) 6-Phenylhexylmalonic acid diethyl ester 22 g of 6-phenylhexylmalonic acid diethyl ester are obtained as a light oil from 24 g of 6-phenylhexyl bromide, 24 g of malonic acid diethyl ester and a solution of 2.6 g of sodium in 150 ml of ethanol by the procedure described in Example 5d.

EXAMPLE 26

2-(5-Phenylpentyl)oxirane-2-carboxylic acid 3 g of sodium 2-(5-phenylpentyl)oxirane-2-carboxylate are thoroughly shaken with 70 ml of ice-cold 1 N hydrochloric acid and 50 ml of diethyl ether; the organic phase is collected, dried over sodium sulfate and concentrated. 1.7 g of the title compound remain as a viscous, colorless oil.

EXAMPLE 27

2-(7-Phenylheptyl)oxirane-2-carboxylic acid ethyl ester (a) 2-(7-Phenylheptyl)oxirane-2-carboxylic acid ethyl ester 1.7 g of the title compound of b.p. 126° to 132° under 0.15 mm Hg are obtained from 4.88 g of 2-methylene-9-phenylnonanoic acid ethyl ester and 6.2 g of m-chloroperbenzoic acid by the procedure described in Example 1a.

(b) 2-Methylene-9-phenylnonanoic acid ethyl ester 5.88 g of 2-methylene-9-phenylnonanoic acid ethyl ester of b.p. 136° under 0.05 mm Hg are obtained from 7.77 g of 7-phenylheptylmalonic acid ethyl ester, 1.08 g of paraformaldehyde, 4.8 ml of pyridine and 0.32 ml of piperidine by the procedure described in Example 1b.

(c) 7-Phenylheptylmalonic acid ethyl ester 7.77 g of 7-phenylheptylmalonic acid ethyl ester are obtained as a viscous oil from 10.2 g of 7-phenylheptylmalonic acid diethyl ester and 1.71 g of potassium hydroxide in 30 ml of ethanol by the procedure described in Example 3c.

(d) 7-Phenylheptylmalonic acid diethyl ester 12.1 g of 7-phenylheptylmalonic acid diethyl ester are obtained as a colorless oil from 17 g of 7-phenylheptyl bromide, 16 g of malonic acid diethyl ester and a solution of 2.0 g of sodium in 100 ml of ethanol by the procedure described in Example 5d.

EXAMPLE 28

2-[(3,4-Dichlorophenyl)propyl]oxirane-2-carboxylic acid ethyl ester (a) 2-[3-(3,4-Dichlorophenyl)propyl]oxirane-2-carboxylic acid ethyl ester 27.0 g of the title compound are obtained as a colorless oil, which is purified by chromatography over a silica gel column (eluant: methylene chloride), from 33.1 g of 5-(3,4-dichlorophenyl)-2-methylenevaleric acid ethyl ester and 45.6 g of m-chloroperbenzoic acid by the procedure described in Example 1a.

(b) 5-(3,4-Dichlorophenyl)-2-methylenevaleric acid ethyl ester 33.1 g of 5-(3,4-dichlorophenyl)-2-methylenevaleric acid ethyl ester of b.p 128° to 130° under 0.02 mm Hg are obtained from 53.9 g of 3-(3,4-dichlorophenyl)propylmalonic acid ethyl ester, 5.4 g of paraformaldehyde, 55 ml of pyridine and 1.7 ml of piperidine by the procedure described in Example 1b.

(c) 3-(3,4-Dichlorophenyl)propylmalonic acid ethyl ester 53.9 g of 3-(3,4-dichlorophenyl)propylmalonic acid ethyl ester are obtained as a light oil from 81 g of 3-(3,4-dichlorophenyl)propylmalonic acid diethyl ester and 14.8 g of potassium hydroxide in 340 ml of ethanol by the procedure described in Example 3c.

(d) 3-(3,4-Dichlorophenyl)propylmalonic acid diethyl ester 79 g of 3-(3,4-dichlorophenyl)propylmalonic acid diethyl ester are obtained as a yellowish oil from 82.1 g of p-toluenesulfonic acid 3-(3,4-dichlorophenyl)-propyl ester, 38.4 g of malonic acid diethyl ester and a solution of 5.3 g of sodium in 400 ml of ethanol by the procedure described in Example 5d.

(e) p-Toluenesulfonic acid 3-(3,4-dichlorophenyl)-propyl ester 175.4 g of p-toluenesulfonic acid 3-(3,4-dichlorophenyl)propyl ester are obtained as a viscous oil from 125 g of 3-(3,4-dichlorophenyl)propan-1-ol, 117.4 g of p-toluenesulfonic acid chloride and 200 ml of pyridine in 600 ml of toluene by the procedure described in Example 5e.

EXAMPLE 29

2-[3-(3,4-Dichlorophenyl)propyl]oxirane-2-carboxylic acid methyl ester 8.0 g of the title compound are obtained as a colorless oil, which is purified by chromatography on silica gel [eluant: methylene chloride/petroleum ether (1:1)], from 19.2 g of 5-(3,4-dichlorophenyl)-2-methylenevaleric acid methyl ester and 27.5 g of m-chloroperbenzoic acid analogously to Example 1a.

The starting compound 5-(3,4-dichlorophenyl)-2-methylenevaleric acid methyl ester (oil) is obtained from 3-(3,4-dichlorophenyl)propylmalonic acid dimethyl ester analogously to Example 3b and 3c.

EXAMPLE 30

2-[3-(5-Chloro-2-methoxyphenyl)propyl]oxirane-2-carboxylic acid ethyl ester (a) 2-[3-(5-Chloro-2-methoxyphenyl)propyl]oxirane-2-carboxylic acid ethyl ester 8.8 g of the title compound are obtained as a colorless oil of b.p. 150° under 0.005 mm Hg from 19.5 g of 5-(5-chloro-2-methoxyphenyl)-2-methylenevaleric acid ethyl ester and 28 g of m-chloroperbenzoic acid in 250 ml of methylene chloride by the procedure described in Example 1a.

(b) 5-(5-Chloro-2-methoxyphenyl)-2-methylenevaleric acid ethyl ester 20.3 g of 5-(5-chloro-2-methoxyphenyl)-2-methylenevaleric acid ethyl ester of b.p. 136° to 140° under 0.01 mm Hg are obtained from 28.5 g of 3-(5-chloro-2-methoxyphenyl)propylmalonic acid ethyl ester, 3.2 g of paraformaldehyde, 16.3 ml of pyridine and 1.1 ml of piperidine by the procedure described in Example 1b.

(c) 3-(5-Chloro-2-methoxyphenyl)propylmalonic acid ethyl ester 28.5 g of 3(5-chloro-2-methoxyphenyl)propylmalonic acid ethyl ester are obtained as a viscous oil from 34.8 g of 3-(5-chloro-2-methoxyphenyl)propylmalonic acid diethyl ester and 6.4 g of potassium hydroxide in 400 ml of ethanol by the procedure described in Example 3c.

(d) 3-(5-Chloro-2-methoxyphenyl)propylmalonic acid diethyl ester 19.1 g of 3-(5-chloro-2-methoxyphenyl)propylmalonic acid diethyl ester of b.p. 136° to 145° under 0.01 mm Hg are obtained from 38 g of 3-(5-chloro-2-methoxyphenyl)propyl chloride, 44 g of malonic acid diethyl ester and a solution of 3.9 g of sodium in 150 ml of ethanol by the procedure described in Example 5d.

(e) 3-(5-Chloro-2-methoxyphenyl)propyl chloride 58.2 g of 3-(5-chloro-2-methoxyphenyl)propan-1-ol and 50 ml of thionyl chloride are stirred at 50° for 8 hours; the excess thionyl chloride is distilled off in vacuo and the residue is distilled under a high vacuum. 50.9 g of 3-(5-chloro-2-methoxyphenyl)propyl chloride of b.p. 87° to 95° under 0.005 mm Hg are obtained.

(f) 3-(5-Chloro-2-methoxyphenyl)propan-1-ol 66.7 g of 3-(5-chloro-2-methoxyphenyl)propan-1-ol of b.p. 94° to 97° under 0.001 mm Hg are obtained from 96.6 g of 3-(5-chloro-2-methoxyphenyl)propionic acid and 14 g of lithium aluminum hydride in 900 ml of diethyl ether by the procedure described in Example 24f.

(g) 3-(5-Chloro-2-methoxyphenyl)propionic acid 63.2 g of 3-(5-2-methoxyphenyl)propionic acid of m.p. 91° to 92° C. are obtained by saponifying 124 g of 5-chloro-2-methoxybenzylmalonic acid diethyl ester with potassium hydroxide and heating the resulting 5-chloro-2-methoxybenzylmalonic acid to 160° to 170° C. 5-Chloro-2-methoxybenzylmalonic acid diethyl ester is obtained from 100 g of 5-chloro-2-methoxybenzyl chloride, 120 ml of malonic acid diethyl ester and a solution of 12.07 g of sodium in 1.1 l of ethanol by the procedure described in Example 24 g.

EXAMPLE 31

2-(8-Phenyloctyl)oxirane 2-carboxylic acid ethyl ester (a) 2-(8-Phenyloctyl)oxirane 2-carboxylic acid ethyl ester 10.4 g of the title compound are obtained as a colorless oil, which is purified by chromatography on silica gel (eluant: methylene chloride), from 11.3 g of 2-methylene-10-phenyldecanoic acid ethyl ester and 16 g of m-chloroperbenzoic acid in 300 ml of methylene chloride by the procedure described in Example 1a.

(b) 2-Methylene-10-phenyldecanoic acid ethyl ester 11.4 g of 2-methylene-10-phenyldecanoic acid ethyl ester are obtained as a colorless oil, which is purified by chromatography on silica gel (eluant: chloroform), from 16.5 g of 8-phenyloctylmalonic acid ethyl ester, 1.65 g of paraformaldehyde, 20 ml of pyridine and 0.5 ml of piperidine by the procedure described in Example 1b.

(c) 8-Phenyloctylmalonic acid ethyl ester 16.7 g of 8-phenyloctylmalonic acid ethyl ester are obtained as a viscous oil from 25.3 g of 8-phenyloctylmalonic acid diethyl ester and 4.6 g of potassium hydroxide in 150 ml of ethanol by the procedure described in Example 3c.

(d) 8-Phenyloctylmalonic acid diethyl ester 25.3 g of 8-phenyloctylmalonic acid diethyl ester are obtained as a yellowish oil from 17.4 g of 8-phenyloctyl chloride, 13 g of malonic acid diethyl ester, a solution of 1.8 g of sodium in 70 ml of ethanol and a pinch of potassium iodide by the procedure described in Example 5d.

(e) 8-Phenyloctyl chloride 17.4 g of 8-phenyloctyl chloride are obtained as a light oil from 16.35 g of 8-phenyloctan-1-ol and 16 ml of thionyl chloride by the procedure described in Example 30e.

EXAMPLE 32

2-[3-(4-tert.-Butylphenyl)propyl]oxirane-2-carboxylic acid methyl ester (a) 2-[3-(4-tert.-Butylphenyl)propyl]oxirane-2-carboxylic acid methyl ester 10.7 g of the title compound are obtained as a colorless oil, which is purified by chromatography on silica gel [eluant: petroleum ether/ethyl acetate (90:10)], from 13 g of 5-(4-tert.-butylphenyl)-2-methylenevaleric acid methyl ester and 17.7 g of m-chloroperbenzoic acid in 300 ml of methylene chloride by the procedure described in Example 1a.

(b) 5-(4-tert.-Butylphenyl)-2-methylenevaleric acid methyl ester 13.1 g of 5-(4-tert.-butylphenyl)-2-methylenevaleric acid methyl ester are obtained as a colorless oil, which is purified by chromatography on silica gel (eluant: methylene chloride) from 18 g of 3-(4-tert.-butylphenyl)propylmalonic acid methyl ester, 1.94 g of paraformaldehyde, 20 ml of pyridine and 0.5 ml of piperidine by the procedure described in Example 1b.

(c) 3-(4-tert.-Butylphenyl)propylmalonic acid methyl ester 18.0 g of 3-(4-tert.-butylphenyl)propylmalonic acid methyl ester are obtained as a viscous oil from 20.9 g of 3-(4-tert.-butylphenyl)propylmalonic acid dimethyl ester and 4.5 g of potassium hydroxide in 140 ml of methanol by the procedure described in Example 3c.

(d) 3-(4-tert.-Butylphenyl)propylmalonic acid dimethyl ester 51.8 g of 3-(4-tert.-butylphenyl)propylmalonic acid dimethyl ester are obtained as a yellowish oil from 64.9 g of p-toluenesulfonic acid 3-(4-tert.-butylphenyl)propyl ester, 26 g of malonic acid dimethyl ester and a solution of 4.74 g of sodium in 250 ml of methanol by the procedure described in Example 5d.

(e) p-Toluenesulfonic acid 3-(4-tert.-butylphenyl)propyl ester 64.9 g of p-toluenesulfonic acid 3-(4-tert.-butylphenyl)propyl ester are obtained as a light yellow oil from 33 g of 3-(4-tert.-butylphenyl)propan-1-ol, 38.5 g of p-toluenesulfonic acid chloride and 65 ml of pyridine in 200 ml of toluene by the procedure described in Example 5e.

EXAMPLE 33

2-[7-(4-Chlorophenyl)heptyl]oxirane-2-carboxylic acid ethyl ester (a) 2-[7-(4-Chlorophenyl)heptyl]oxirane-2-carboxylic acid ethyl ester 6.13 g of the title compound of b.p. 140° to 148° under 0.005 mm Hg are obtained from 10.0 of 9-(4-chlorophenyl)-2-methylenenonanoic acid ethyl ester and 13.15 g of m-chloroperbenzoic acid in 50 ml of methylene chloride by the procedure described in Example 1a.

(b) 9-(4-Chlorophenyl)-2-methylenenonanoic acid ethyl ester 15.9 g of 9-(4-chlorophenyl)-2-methylenenonanoic acid ethyl ester are obtained as a colorless oil of b.p. 134° to 136° under 0.005 mm Hg from 33 g of 7-(4-chlorophenyl)heptylmalonic acid ethyl ester, 4.1 g of paraformaldehyde, 17.8 ml of pyridine and 1.2 ml of piperidine by the procedure described in Example 1b.

(c) 7-(4-Chlorophenyl)heptylmalonic acid ethyl ester 33.62 g of 7-(4-chlorophenyl)heptylmalonic acid ethyl ester are obtained as a viscous oil from 37.37 g of 7-(4-chlorophenyl)heptylmalonic acid diethyl ester and 6.56 g of potassium hydroxide in 100 ml of ethanol by the procedure described in Example 3c.

(d) 7-(4-Chlorophenyl)heptylmalonic acid diethyl ester 37.37 g of 7-(4-chlorophenyl)heptylmalonic acid diethyl ester of b.p. 160° to 165° under 0.005 mm Hg are obtained from 33.0 g of 7-(4-chlorophenyl)heptyl bromide, 27.36 g of malonic acid diethyl ester and a solution of 2.62 g of sodium in 200 ml of ethanol by the procedure described in Example 5d.

(e) 7-(4-Chlorophenyl)heptyl bromide 30 g of 7-(4-chlorophenyl)heptan-1-ol, 0.13 g of red phosphorus and 37 ml of 62% strength hydrogen bromide are boiled for 6 hours, 8 ml of concentrated sulfuric acid are then added dropwise and the mixture is boiled again for 6 hours. The reaction mixture is poured into 100 ml of ice-water and is extracted twice with diethyl ether; the ether extracts are concentrated and the residue is distilled. 33.5 g of 7-(4-chlorophenyl)heptyl bromide of b.p. 125° to 127° under 0.1 mm Hg are obtained.

(f) 7-(4-Chlorophenyl)heptanol 31.2 g of 7-(4-chlorophenyl)heptanol of b.p. 140° under 0.3 mm Hg are obtained from 51 g of 7-(4-chlorophenyl)heptanoic acid and 8.0 g of lithium aluminum hydride in 500 ml of diethyl ether by the procedure described in Example 24f.

(g) 7-(4-Chlorophenyl)heptanoic acid 80 g of 5-(4-chlorophenyl)pentylmalonic acid ethyl ester are boiled under reflux with 45 g of potassium hydroxide in 230 ml of water and 100 ml of ethanol for 5 hours; after cooling, the mixture is adjusted to pH 1–2 with concentrated hydrochloric acid and is extracted 3 times with diethyl ether. The combined organic solutions are concentrated and the residue [5-(4-chlorophenyl)pentylmalonic acid] is heated to 160° for 3.5 hours. The residue consists of 51 g of 7-(4-chlorophenyl)heptanoic acid of m.p. 75° to 78°.

EXAMPLE 34

Calcium-2-(5-phenylpentyl)oxirane-2-carboxylate

A solution of 400 mg calcium chloride in 5 ml of water is added dropwise to a solution of 1.0 g of sodium 2-(5-phenylpentyl)oxirane-2-carboxylate in 30 ml of water. The mixture is stirred thoroughly. The solution is decanted from the viscous precipitate which has separated out. The precipitate is stirred again with water and decanted. After drying over phosphorus pentoxide 820 mg of the title compound (softening at 270° C. and melting at about 300° C. under decomposition) are obtained.

EXAMPLE 35

2-(3-Phenylpropyl)oxirane-2-carboxylic acid sec.-butyl ester (a) 2-(3-Phenylpropyl)oxirane-2-carboxylic acid sec.-butyl ester 6.1 g of the title compound [almost colorless oil; purified by chromatography on a silica gel column (eluant: petroleum ether/ethyl acetate 9:1)] are obtained from 10 g of 2-methylene-5-phenylvaleric acid sec.-butyl ester and 18 g of m-chloroperbenzoic acid in 200 ml of methylene chloride by the procedure described in Example 1a.

(b) 2-Methylene-5-phenylvaleric acid sec.-butyl ester 27 g of 2-methylene-5-phenylvaleric acid chloride are added dropwise to a solution of 100 ml of sec.-butanol and 20 ml of triethylamine in 300 ml of diethyl ether at 25° to 30°. When the addition is complete, the obtained mixture is stirred at room temperature for another hour; 500 ml of ice water are then added and the mixture is shaken thoroughly. The organic phase is collected, dried over sodium sulfate and concentrated. 19.5 g of 2-methylene-5-phenylvaleric acid sec.-butyl ester (b.p. 115° to 126° under 0.01 mm Hg) are obtained.

(c) 2-Methylene-5-phenylvaleric acid chloride 25 g of 2-Methylene-5-phenylvaleric acid and 20 ml of thionyl chloride (freshly distilled) are stirred at 50° for 6 hours. Subsequently, excess thionyl chloride is distilled off in vacuo. 27 g of 2-methylene-5-phenylvaleric acid chloride remain as a brown liquid which is used without further purification.

EXAMPLE 36

2-[3-(4-Chlorophenyl)propyl]oxirane-2-carboxylic acid isopropyl ester (a) 2-[3-(4-Chlorophenyl)propyl]oxirane-2-carboxylic acid isopropyl ester 5.4 g of the title compound [yellowish oil; purified by chromatography on a silica gel colunm (eluant: petroleum ether/ethyl acetate 9:1)] are obtained from 12 g of 5-(4-chlorophenyl)-2-methylenevaleric acid isopropyl ester and 20 g of m-chloroperbenzoic acid in 150 ml of methylene chloride by the procedure described in Example 1a.

(b) 5-(4-Chlorophenyl)-2-methylenevaleric acid isopropyl ester 12.2 g of 5-(4-chlorophenyl)-2-methylenevaleric acid isopropyl ester (b.p. 128° to 134° under 0.01 mm Hg) are obtained from 21.5 g of 5-(4-chlorophenyl)-2-methylenevaleric acid chloride, 100 ml of isopropanol and 18 ml of triethylamine in 300 ml of diethyl ether by the procedure described in Example 35b.

(c) 5-(4-Chlorophenyl)-2-methylenevaleric acid chloride 21.5 g of 5-(4-chlorophenyl)-2-methylenevaleric acid chloride (brown oil) are obtained from 20.5 g of 5-(4-chlorophenyl)-2-methylenevaleric acid and 20 ml of thionyl chloride by the procedure described in Example 35c.

(d) 5-(4-Chlorophenyl)-2-methylenevaleric acid 25 g of 5-(4-chlorophenyl)-2-methylenevaleric acid ethyl ester, 100 ml of a 2 N sodium hydroxide solution and 50 ml of ethanol are stirred at 50° for 3 hours. After cooling, 100 ml of 2 N hydrochloric acid are added slowly, while cooling with ice, to the reaction mixture which is then extracted 4 times, with 50 ml of diethyl ether each time. The united organic phases are washed with water, dried over sodium sulfate and concentrated. 20.5 g of 5-(4-chlorophenyl)-2-methylenevaleric acid remain as a brown oil.

EXAMPLE 37

Batch for ampoules 1,000 g of 2-[3-(4-chlorophenyl)propyl]oxirane-2-carboxylic acid are dissolved in about 80 liters of doubly-distilled water, the equivalent amount of sodium hydroxide solution being added. The solution is adjusted to pH 7.0±0.5 and made up to 100 liters with doubly-distilled water. It is then filtered under sterile conditions and filled into 2 ml ampoules under germ-free conditions.

EXAMPLE 38

100,000 capsules with an active compound content of 30 mg are prepared from the following constituents:

3,000 g of 2-(4-phenylbutyl)oxirane-2-carboxylic acid ethyl ester are mixed with 5,000 g of neutral oil, and the mixture is filled into soft gelatin capsules.

EXAMPLE 39

10,000 capsules with an active compound content of 25 mg are prepared as follows:

250 g of 2-[3-(3-chlorophenyl)propyl]oxiranecarboxylic acid ethyl ester are dissolved in 1,000 ml of methylene chloride. The solution is mixed thoroughly with 750 g of micronized silicic acid. The mixture is evaporated to dryness and then filled into hard gelatin capsules.

EXAMPLE 40

10,000 capsules with an active compound content of 20 mg are prepared from the following constituents:

200 g of 2-[3-(3-trifluoromethylphenyl)propyl]oxirane-2-carboxylic acid ethyl ester are dissolved in 1,000 ml of methylene chloride. The solution is mixed thoroughly with 800 g of micronized silicic acid. The mixture is evaporated to dryness and then filled into hard gelatin capsules.

EXAMPLE 41

10,000 capsules with an active compound content of 25 mg are prepared as follows:

250 g of 2-[5-(4-chlorophenyl)pentyl]oxirane-2-carboxylic acid ethyl ester are dissolved in 1,000 ml of methylene chloride. The solution is mixed thoroughly with 750 g of micronized silicic acid. The mixture is evaporated to dryness and then filled into hard gelatin capsules.

EXAMPLE 42

Tablets with an active compound content of 25 mg are prepared as follows:

10 kg of sodium 2-[5-(4-chlorophenyl)pentyl]oxirane-2-carboxylate, 45 kg of xylit and 30 kg of calcium phosphate are granulated with 2.5 kg of polyvinylpyrrolidone (molecular weight ∼25,000) in approximately 6 liters of water. The granulate is sieved through a sieve of 1.25 mm mesh size and, after drying, 9 kg of carboxymethylcellulose, 2.5 kg of talc and 1 kg of magnesium stearate are added. The dry granulate is compressed into tablets of 8 mm diameter, 250 mg weight and a hardness of 5-6 kg.

PHARMACOLOGY

The substituted oxiranecarboxylic acids of the general formula I according to the invention lower the level of glucose and of ketones in the blood, their chemical structure differs from that of beta-cytotropic substances which have an action on the pancreas (for example sulfonylureas), and their mode of action differs fundamentally from that of these substances in that they have an extra-pancreatic action, and they prove to be superior to commercial preparations having an extra-pancreatic action (for example Buformin and Phenformin).

In the Tables below, the compounds investigated are characterized by a serial number, which is allocated as follows:

| Serial No. | Name of compound |
| --- | --- |
| 1 | Buformin |
| 2 | Phenformin |
| 3 | 2-[3-(4-Chlorophenyl)-propyl]oxirane-2-carboxylic acid ethyl ester |
| 4 | 2-[3-(4-Chlorophenyl)-propyl]oxirane-2-carboxylic acid (sodium salt) |

-continued

| Serial No. | Name of compound |
|---|---|
| 5 | 2-[3-(3-Trifluoromethylphenyl)-propyl]oxirane-2-carboxylic acid ethyl ester |
| 6 | 2-[3-(3-Trifluoromethylphenyl)-propyl]oxirane-2-carboxylic acid (sodium salt) |
| 7 | 2-(5-Phenyl-pentyl)oxirane-2-carboxylic acid ethyl ester |
| 8 | 2-(5-Phenyl-pentyl)oxirane-2-carboxylic acid (sodium salt) |
| 9 | 2-[5-(4-Chlorophenyl)-pentyl]oxirane-2-carboxylic acid ethyl ester |
| 10 | 2-[5-(4-Chlorophenyl)-pentyl]oxirane-2-carboxylic acid (sodium salt) |
| 11 | 2-(4-Phenylbutyl)oxirane-2-carboxylic acid ethyl ester |
| 12 | 2-[3-(3-Chlorophenyl)-propyl]oxirane-2-carboxylic acid ethyl ester |
| 13 | 5-(4-Chlorophenyl)-2-methylenevaleric acid ethyl ester |
| 14 | 5-(3-Chlorophenyl)-2-methylenevaleric acid ethyl ester |
| 15 | 2-Methylene-7-phenylheptanoic acid ethyl ester |

Table I reflects investigations of the effect of representative compounds according to the invention on the blood glucose concentration of fasting, metabolically healthy rats which is observed in the course of 5 hours after single oral administration of 0.056 to 0.6 mmol of substance/kg of body weight.

Column A states the dose of active compound (mg/kg) which effects in 50% of the animals a lowering of the blood glucose concentration by at least 25% with reference to the control group. Column B states the dose of active compound (mg/kg) which effects in 50% of the animals a lowering of the blood glucose concentration by at least 15% with reference to the control group. Column C provides data relating to acute toxicity ($LD_{50}$; mice, peroral administration).

TABLE I

| Serial No. | A<br>$ED_{50}$ (25%)<br>[mg/kg]<br>rats p.o. | B<br>$ED_{50}$ (15%)<br>[mg/kg]<br>rats p.o. | C<br>$LD_{50}$[mg/kg]<br>mice p.o. |
|---|---|---|---|
| 1 | 194 | >100 | 475 |
| 2 | >343 | >150 | 410* |
| 3 | 54 | 40 | 730 |
| 4 | 41 | 20 | |
| 5 | 24 | 6 | ~300 |
| 6 | 23 | 14 | |
| 7 | 21** | 10 | 230 |
| 8 | 12 | 2 | |
| 9 | 24 | 3 | 275 |
| 10 | 16 | 5 | |
| 11 | | 67 | |
| 12 | | 59 | |

Re Table I:
*Cited according to Blickens, D. A.; Riggi, S. J.: Toxicol.Appl.Pharmacol. 14(1969)393-400
**$ED_{50}$ (23%)
Column A = dose, which effects a lowering of the blood glucose concentration by 25% in 50% of the animals
Column B = dose, which effects a lowering of the blood glucose concentration by 15% in 50% of the animals
Column C = acute toxicity ($LD_{50}$ in mg/kg; mice, peroral administration)

The α-methylenecarboxylic acids, appearing as intermediates within the scope of the invention, also reveal in vivo a hypoglycemic action as follows from Table II.

TABLE II

| Serial No. | B<br>$ED_{50}$ (15%) [mg/kg]<br>rats p.o. |
|---|---|
| 13 | 252 |
| 14 | >253 |
| 15 | 80 |

Re Table II:
Column B = dose, which effects a lowering of the blood glucose concentration by 15% in 50% of the animals.

Table III reflects investigations of the effect of representative compounds according to the invention on the blood glucose concentration of fasting, metabolically healthy guinea pigs which is observed in the course of 5 hours after single oral administration of 0.056 to 0.6 mmol of substance/kg of body weight.

Column A states the dose of active substance (mg/kg) which effects in 50% of the animals a lowering of the blood glucose concentration by at least 25% with reference to the control group. Column B states the dose of active substance (mg/kg) which effects in 50% of the animals a lowering of the blood glucose concentration by at least 15% with reference to the control group. Column C provides data relating to acute toxicity ($LD_{50}$; guinea pig, peroral administration).

TABLE III

| Serial No. | A<br>$ED_{50}$ (25%)<br>[mg/kg]<br>guinea pig p.o. | B<br>$ED_{50}$ (15%)<br>[mg/kg]<br>guinea pig p.o. | C<br>$LD_{50}$[mg/kg]<br>guinea pig p.o. |
|---|---|---|---|
| 1 | 40-50** | — | 58* |
| 2 | 20-25*** | — | 47* |
| 3 | 22 | 11 | — |
| 4 | 26 | 12 | 500-600 |
| 5 | <24 | 3 | — |
| 6 | 11 | 6 | 300-400 |
| 7 | 21 | 11 | — |
| 8 | 7 | 3 | 500-600 |
| 9 | <24 | 5 | — |
| 10 | 8 | 3 | 300-400 |

Re Table III:
*cited according to Proske, G.; Osterloh, G.; Beckmann, R. Lagler, F.; Michael, G.; Muckter, H.: Arzneim.Forsch. 12(1962)314-318.
**cited according to Beckmann, R.: unpublished studies 1960 in Hdb.exp.Pharmakol. XXIX, p.477, Springer, Berlin 1971.
***cited according to Ungar, G.; Freeman, L.; Schapiro, S. L. Proc.Soc.exp.Biol. (N.Y.) 95(1957)190-192.
Column A = dose, which effects a lowering of the blood glucose concentration by 25% in 50% of the animals
Column B = dose, which effects a lowering of the blood glucose concentration by 15% in 50% of the animals
Column C = acute toxicity ($LD_{50}$ in mg/kg; guinea pig, peroral administration, preliminary results).

In relation to the comparison compounds, the compounds according to the invention are distinguished by a lower toxicity or better therapeutic breadth and by a more powerful hypoglycemic action.

The pharmacological properties were determined by the following methods:

1. Determination of glucose in the blood after a single oral administration

Young male Sprague-Dawley rats (body weight: 150-200 g) and young cross-bred male guinea pigs (body weight: 250-300 g) are used. The animals are kept in Makrolon cages with up to 4 animals per cage (ambient temperature: 23° C., relative atmospheric humidity: 55%, fixed day/night rhythm [12/12 hours], standard diet: Altromin ®). The rats (guinea pigs) are deprived of the feed 18 (42) hours before the first sample of blood is taken. Water is available ad libitum. Samples of blood are taken from the postorbital plexus by puncture immediately before 3 and 5 hours after administration of the substance.

After deproteinization with perchloric acid, the glucose in the blood is determined by means of the enzymatic HK/G-6-PDH method of R. Richterich [Klinische Chemie, Theorie und praxis, (Clinical Chemistry, Theory and Practice), 3rd edition, 1971, S. Karger Verlag, Zurich-Basle, page 275]. A control group (treated with pure solvent) is also investigated in each case for comparison.

2. Determination of the toxicity

The toxicity investigations are carried out on female NMRI mice (body weight: 22 to 26 g). 18 hours before the treatment, the feed (Altromin ®) for the animals (5 animals per dose) is reduced to 50 g/50 animals and water is available ad libitum. Various doses of the substances (volume: 10 ml/kg) are administered orally by means of a stomach tube. The observation time is 7 days. The $LD_{50}$, that is to say the dose at which 50% of the animals die, is determined graphically from the dose/response curve.

Attention is drawn to the fact that the toxicity data determined are influenced by the state of nourishment of the animals used, e.g. the $LD_{50}$ p.o. of rats, which are deprived of the feed only 4 hours, is above 1 g/kg of body weight.

The invention and its advantages are readily understood from the preceding description. Various changes may be made in the synthesis, the intermediates, the pharmacologically-active final products, the dosage forms, the medicament compositions, the mode of administration and treatment regimes without departing from the spirit and scope of the invention or sacrificing its material advantages. The hereinbefore described aspects of the subject invention are merely illustrative of preferred embodiments.

What is claimed is:

1. A substituted oxiranecarboxylic acid of the formula

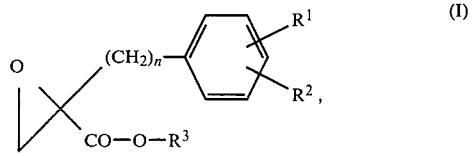

wherein
 $R^1$ is —H, halo, hydroxyl, lower alkyl, lower alkoxy or trifluoromethyl,
 $R^2$ has one of the meanings of $R^1$,
 $R^3$ is —H or lower alkyl and
 n is an integer from 1 to 8, inclusive,
or a salt of each carboxylic acid.

2. A substituted oxiranecarboxylic acid according to claim 1,
wherein
 $R^1$ and $R^2$ are in the meta-position or para-position,
 $R^1$ is —H, chloro, methyl, methoxy or trifluoromethyl,
 $R^2$ is —H or chloro,
 $R^3$ is —H or lower alkyl and
 n is an integer from 3 to 7, inclusive, or a salt of each carboxylic acid with a base.

3. A compound according to claim 2, wherein n is an integer from 3 to 5, inclusive.

4. A substituted oxiranecarboxylic acid according to claim 1,
wherein
 $R^1$ and $R^2$ are in the meta-position or para-position,
 $R^1$ is —H, chloro or trifluoromethyl,
 $R^2$ is —H,
 $R^3$ is —H, methyl or ethyl and
 n is 3 or 4,
or a pharmacologically-acceptable salt of each carboxylic acid with an inorganic or organic base.

5. A compound according to claim 4, wherein $R^1$ is —H or chloro.

6. A compound according to claim 4, wherein $R^1$ is trifluoromethyl.

7. A substituted oxiranecarboxylic acid according to claim 1,
wherein
 $R^1$ and $R^2$ are in the meta-position or para-position,
 $R^1$ is —H, chloro or trifluoromethyl,
 $R^2$ is —H,
 $R^3$ is —H, methyl or ethyl and
 n is 5,
or a pharmacologically-acceptable salt of each carboxylic acid with an inorganic or organic base.

8. A substituted oxiranecarboxylic acid according to claim 1,
wherein
 $R^1$ is —H, halo, hydroxyl, lower alkyl, lower alkoxy or trifluoromethyl,
 $R^2$ has one of the meanings of $R^1$,
 $R^3$ is —H or lower alkyl and
 n is an integer from 1 to 5, inclusive,
or a pharmacologically-acceptable salt of each acid with an inorganic or organic base.

9. A compound according to claim 1 which is 2-[3-(4-chlorophenyl)propyl]oxirane-2-carboxylic acid ethyl ester.

10. A compound according to claim 1 which is 2-[3-(4-chlorophenyl)propyl]oxirane-2-carboxylic acid and the pharmacologically-acceptable salts of this acid.

11. A compound according to claim 1 which is 2-[3-(3-chlorophenyl)propyl]oxirane-2-carboxylic acid ethyl ester.

12. A compound according to claim 1 which is 2-[3-(3-chlorophenyl)propyl]oxirane-2-carboxylic acid and the pharmacologically-acceptable salts of this acid.

13. A compound according to claim 1 which is 2-[3-(3-trifluoromethylphenyl)propyl]oxirane-2-carboxylic acid ethyl ester.

14. A compound according to claim 1 which is 2-[3-(3-trifluoromethylphenyl)propyl]oxirane-2-carboxylic acid and the pharmacologically-acceptable salts of this acid.

15. A compound according to claim 1 which is 2-(5-phenylpentyl)oxirane-2-carboxylic acid ethyl ester.

16. A compound according to claim 1 which is 2-(5-phenylpentyl)oxirane-2-carboxylic acid and the pharmacologically-acceptable salts of this acid.

17. A compound according to claim 1 which is 2-[5-(4-chlorophenyl)pentyl]oxirane-2-carboxylic acid ethyl ester.

18. A compound according to claim 1 which is 2-[5-(4-chlorophenyl)pentyl]oxirane-2-carboxylic acid and the pharmacologically-acceptable salts of this acid.

19. A medicament composition comprising physiologically-acceptable excipient in combination with from 2 to 200 milligrams per unit dose of a pharmacologically-acceptable compound of one of claims 1 to 18.

20. A medicament composition for the prophylaxis or treatment of a glucose or fat metabolism disorder which comprises physiologically-acceptable excipient in combination with an effective amount of a pharmacologically-acceptable compound of one of claims 1 to 18.

21. A method for the prophylaxis or treatment of a glucose or fat metabolism disorder which comprises administering an effective amount of a pharmacologically-acceptable compound according to one of claims 1 to 18 to a mammal subject to or afflicted with such disorder.

* * * * *

UNITED STATES PATENT AND TRADEMARK OFFICE
CERTIFICATE OF CORRECTION

PATENT NO. : 4,324,796

DATED : April 13, 1982

INVENTOR(S) : Klaus EISTETTER and Erich RAPP

It is certified that error appears in the above-identified patent and that said Letters Patent are hereby corrected as shown below:

Title page, at [30], "[SU] U.S.S.R." should read --[CH] Switzerland--; at [56], under "FOREIGN PATENT DOCUMENTS", "8/1979" should read --8/1980--. Column 1, line 19, "10" should read --*10*--; line 23, "45" should read --*45*--. Column 2, line 23, "metaposi-" should read --meta-posi- --. Column 3, line 66, "ester." should read --ester,--. Column 4, lines 24 and 25, "ethyl ester ... thereof." should read --
    ethyl ester,
the corresponding oxirane-2-carboxylic acids and pharmacologically-acceptable salts thereof.--; line 43, "accompagnied" should read --accompanied--. Column 8, line 24, "e.g," should read --e.g.,--. Column 10, line 31, "1 N" should read --1N--. Column 11, line 47, "3-(2-chlorophenyl)acid" should read --3-(2-chlorophenyl)propylmalonic acid--. Column 12, line 53, "10.0 g" should read --10.0 g of--. Column 15, line 11, "(c) Phenylpentylmalonic" should read --(c) 5-Phenylpentylmalonic--; line 12, "44.8" should read --44.8 g--. Column 16, line 33, "Phenylmethyl" should read --Phenylethyl--; line 68, "propyltosylate" should read --propyl tosylate--. Column 18, line 37, "25.7 g" should start a new paragraph; "Fluorophenyl" should read --fluorophenyl--. Column 19, line 33, "fluorobenzylmalonic" should read --fluorobenzyl-malonic--. Column 20, line 18, "132°" should read --132° C--; line 43, "2-[(3,4-" should read --2-[3-(3,4- --. Column 21, line 5, ")-propyl" should read --)propyl--; line 53, "3(5-" should read --3-(5- --. Column 22, line 13, "5-2" should read --(5-chloro-2- --. Column 23, line 11, "chloride)" should read --chloride),--. Column 23, line 45, "10.0" should read --10.0 g--. Column 24, line 24, "100" should read --110--. Column 25, line 18, "colunm" should read --column--; line 41, "2 N" should read --2N--; line 44, "2 N" should read --2N--. Column 26, lines 66 and 67, ")-propyl" (each occurrence) should read --)propyl--. Column 27, lines 4, 6 and 18, ")-propyl" (each occurrence) should read --)propyl--; lines 8, 10, 12 and 14, ")-pentyl" (each occurrence) should read --)pentyl--; line 58, "14" should read --*14*--. Column

UNITED STATES PATENT AND TRADEMARK OFFICE
CERTIFICATE OF CORRECTION

PATENT NO. : 4,324,796

DATED : April 13, 1982

INVENTOR(S) : Klaus EISTETTER and Erich RAPP

It is certified that error appears in the above–identified patent and that said Letters Patent are hereby corrected as shown below:

28, line 41, "Beckmann, R." should read --Beckmann, R.;--; line 42, "12" should read --*12*--; line 44, "S. L." should read --S. L.;--; line 45, "95" should read --*95*--. Column 29, line 6, "praxis" should read --Praxis--.

Signed and Sealed this

Nineteenth Day of October 1982

[SEAL]

Attest:

GERALD J. MOSSINGHOFF

Attesting Officer   Commissioner of Patents and Trademarks